United States Patent [19]

Hioki et al.

[11] Patent Number: 5,164,179

[45] Date of Patent: Nov. 17, 1992

[54] BIOCIDE ACTIVATOR

[75] Inventors: Yuichi Hioki; Kazuhiko Kurita; Tetsuji Iwasaki, all of Wakayama, Japan

[73] Assignee: Kao Corporation, Tokyo, Japan

[21] Appl. No.: 639,529

[22] Filed: Jan. 10, 1991

[30] Foreign Application Priority Data

Apr. 16, 1990 [JP] Japan .................................. 2-99863

[51] Int. Cl.$^5$ ..................... A61K 31/785; A61K 31/74
[52] U.S. Cl. .............................. 424/78.08; 424/78.35; 424/78.31
[58] Field of Search ............. 424/81, 78, 78.08, 78.31, 424/78.35

[56] References Cited

U.S. PATENT DOCUMENTS

| | | | |
|---|---|---|---|
| 3,577,516 | 5/1971 | Gould et al. | 424/45 |
| 4,374,126 | 2/1983 | Cardarelli et al. | 424/81 |
| 4,883,828 | 11/1989 | Oakes et al. | 424/81 |
| 4,885,159 | 12/1989 | Miyake et al. | 424/81 |

Primary Examiner—Thurman K. Page
Assistant Examiner—Peter F. Kulkosky
Attorney, Agent, or Firm—Birch, Stewart, Kolasch & Birch

[57] ABSTRACT

The biocidal effect of a biocide can be enhanced with the use of an effective amount of the auxiliary compound having the formula (I).

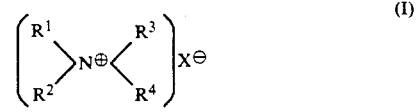

wherein at least one of $R^1$, $R^2$, and $R^3$ represents a straight-chain or branched alkyl or alkenyl group having 8 to 30 carbon atoms while other(s) represent a group or a combination selected from among

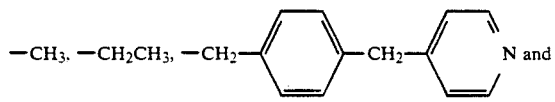

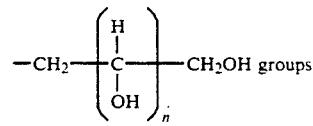

wherein n ranges from 1 to 5;
$R^4$ represents a —CH$_3$ or —CH$_2$CH$_3$ group; and
a counter ion $X^\ominus$ is an anion residue of an acid of an anionic oligomer or polymer having an average molecular weight of from 300 to 20,000.

3 Claims, No Drawings

BIOCIDE ACTIVATOR

FIELD OF INVENTION

This invention relates to an agrohorticultural biocide activator. More particularly, it relates to an agrohorticultural biocide activator whereby the dose of an agricultural chemical can be reduced and the expression of the resistance of disease and insect pests against agricultural chemicals can be suppressed.

PRIOR ART

A common problem for agrohorticultural biocides which include bactericides, insecticides, acaricides and herbicides, and which act by inhibiting a specific enzyme system/metabolic system is the frequent occurrence of disease and insect resistant pests. As a result, it is necessary to apply larger and larger amounts of the biocide which eventually becomes impossible.

On the other hand, a biocide having a low basic activity should be applied in a large amount in order to completely control diseases and insect pests. However the application of a large amount of an agricultural chemical not only causes environmental pollution but also restricts the range of available agricultural chemicals. Therefore it has been necessary to develop a highly safe chemical which can suppress the expression of the resistance of disease and insect pests and enhance the effect of an agricultural chemical.

SUMMARY OF THE INVENTION

In order to enhance the effect of a biocide and to suppress the occurrence of a disease and insect resistant pests, the present inventors have conducted extensive studies. As a result, they have found that a compound, which is obtained by substituting a counter ion of a quaternary ammonium salt with an anion residue of an acid of an anionic oligomer or polymer having a molecular weight of from 300 to 20,000, can enhance the effect of a biocide and remarkably improve its effect on disease and insect pests that are resistant to various biocides without subjecting the plants any chemical injury.

Accordingly, the present invention provides a biocide activator which comprises a compound represented by the following general formula (I) as an essential ingredient:

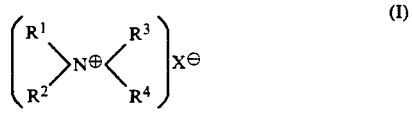

wherein at least one of $R^1$, $R^2$ and $R^3$ represents a straight-chain or branched alkyl or alkenyl group having 8 to 30 carbon atoms while other(s) represent a group or a combination selected from among

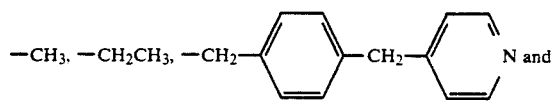

-continued

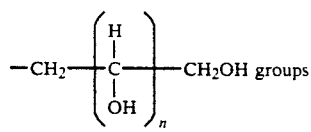

(wherein n ranges from 1 to 5;
$R^4$ represents a $-CH_3$ or $-CH_2CH_3$ group; and a counter ion $X^\ominus$ is an anion residue of an acid of an anionic oligomer or polymer having an average molecular weight of from 300 to 20,000.

The biocidal effect of a biocide can be enhanced with the use of an effective amount of an auxiliary compound having the formula (I).

The invention moreover provides a biocide composition which comprises a biocide and the auxiliary compound and an aqueous biocide solution or suspension which comprises a biocidally effective amount of a biocide and, the auxiliary compound. The invention additionally provides a biocidal effect-enhancing agent comprising the compound as above defined.

It is preferable that the solution or suspension comprises 0.01 to 60 percent by weight of the auxiliary compound.

It is preferable that the anionic oligomer or polymer is selected from the below shown groups (1) to (3) shown below.

The anionic oligomer or polymer to be used in the present invention may preferably comprises one or more compounds selected from among the following compounds 1) to 3):

1) a polymer comprising one or more monomers selected from among unsaturated carboxylic acids and derivatives thereof as an essential component;
2) a polymer comprising styrenesulfonic acid as an essential constituting monomer; and
3) a formalin condensate of a sulfonate of a polycyclic aromatic compound optionally having a hydrocarbon group as a substituent.

The quaternary ammonium salt represented by the general formula (I) relating to the present invention is characterized by its counter ion. Namely, it is important in the present invention that the counter ion $X^\ominus$ be an anion residue of an acid of an anionic oligomer or polymer having a molecular weight of from 300 to 20,000 and that said anionic oligomer or polymer have an anion residue of an acid which may fundamentally produce the counter ion $X^\ominus$. The anionic oligomers or polymers to be used in the present invention, as specified in the above items 1) to 3), will now be described in detail.

1) A polymer comprising one or more monomers selected from among unsaturated carboxylic acids and derivatives thereof as an essential component.

Examples of the monomer to be used in the preparation of the polymer 1) include unsaturated monocarboxylic acids such as acrylic acid and methacrylic acid, unsaturated dicarboxylic acid such as maleic acid and derivatives thereof such as alkyl esters of the above-mentioned acid (for example, methyl esters) and polyoxyethylene esters. In addition to these monomers, copolymerizable monomers such as vinyl acetate, isobutylene, diisobutylene and styrene may be used.

These monomers may be polymerized by a conventionally known method. Neither the ratio of the monomers nor the degree of polymerization is particularly restricted.

Particular examples thereof include polyacrylic acid, polymethacrylic acid, acrylic acid/methacrylic acid copolymer, acrylic acid/polyoxyethylene methacrylate copolymer, acrylic acid/methyl acrylate copolymer, acrylic acid/vinyl acetate copolymer, acrylic acid/maleic acid copolymer, maleic acid/isobutylene copolymer and maleic acid/styrene copolymer. Two or more polymers selected among the above-mentioned ones may be employed. Furthermore, they may be converted into salts of alkali metals, ammonia or organic amines in a manner so as not to deteriorate the performance thereof.

2) A polymer comprising styrenesulfonic acid as an essential constituting monomer.

The homopolymer of styrenesulfonic acid may be easily prepared by polymerizing styrenesulfonic acid or by sulfonating polystyrene. Styrenesulfonic acid polymer has a skeleton represented by the following formula:

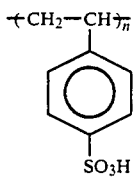

The molecular weight thereof may range from 300 to 20,000, preferably from 300 to 10,000.

On the other hand, a copolymer of styrenesulfonic acid with other monomer(s) may be easily prepared by copolymerizing styrenesulfonic acid with the monomer(s) or by sulfonating a copolymer of styrene with other monomer(s). Examples of the monomers to be copolymerized include hydrophobic monomers such as alkyl acrylates, alkyl methacrylates, vinyl alkyl ethers, vinyl acetate, ethylene, propylene, butylene, butadiene, diisobutylene, vinyl chloride, vinylidene chloride, acrylonitrile and styrene and hydrophilic ones such as acrylic acid, methacrylic acid, maleic acid, fumaric acid, maleic anhydride, vinyl alcohol, acrylamide, methacrylamide, diacetone acrylamide, N-vinylpyrrolidone, 2-acrylamido-2-methylpropanesulfonic acid, methacrylsulfonic acid, xylenesulfonic acid and naphthalenesulfonic acid. Preferable examples of the copolymer include (meth)acrylic acid/styrenesulfonic acid copolymer. The molar ratio of the (meth)acrylic acid to the styrenesulfonic acid in the copolymer may range from 1/10 to 10/1, preferably from 1/3 to 4/1. The average molecular weight of the copolymer may range from 300 to 20,000, preferably from 1,000 to 10,000. The copolymer may further contain a neutralized portion of a salt such as sodium salt, potassium salt, ammonium salt, diethanolamine salt, triethanolamine salt, monoisopropanolamine salt, diisopropanolamine salt, triisopropanolamine salt or 2-amino-2-methylpropane-1,3-diol salt, so long as the performance of the copolymer does not thereby deteriorate.

3) A formalin condensate of a sulfonate of a polycyclic aromatic compound optionally having a hydrocarbon group as a substituent.

Particular examples thereof include formalin condensates of petroleum sulfonic acid derivatives, ligninsulfonic acid derivatives, naphthalenesulfonic acid derivatives, xylenesulfonic acid derivatives and alkylbenzenesulfonic acid derivatives.

The above-mentioned compound 3) relating to the present invention may be obtained by, for example, sulfonating a compound such as naphthalene, an alkyl-substituted benzene, an alkyl-substituted naphthalene, anthracene, an alkyl-substituted anthracene, lignin or a compound contained in a petroleum residue having an aromatic ring by a conventional method and then condensing the obtained sulfonate with formalin. In this case, the degree of condensation may be preferably 2 or above, still preferably from 3 to 30. When the molecular weight of the obtained condensate is smaller than 300, the condensation can produce only a limited effect, which in practice causes some problems.

The aromatic compound to be used in the above process may be selected from among various ones. Preferable examples thereof include lignin, xylene, toluene, naphthalene and alkyl-naphthalenes having an alkyl group of 1 to 6 carbon atoms. As a matter of course, a mixture thereof may be employed.

Furthermore, a salt of an alkali metal such as sodium or potassium, an alkaline earth metal such as calcium, and an amine or ammonium may be used, so long as the performance of the resulting compound does not thereby deteriorate.

The quaternary ammonium salt represented by the general formula (1) relating to the present invention may be easily prepared by, for example, preliminarily converting a quaternary ammonium salt having a halogen atom as a counter ion into a quaternary ammonium of OH-type by using an ion exchange resin and then neutralizing the resulting product with an oligomer or a polymer having an anion residue of the acid as described above. Furthermore, it may contain an alkali metal salt, an amine salt or an organic amine salt, so long as the performance thereof does not deteriorated thereby.

The biocide activator of the present invention may be mixed and diluted with a biocide and then applied to plants or soil. In the application thereof, it is preferable to use the above-mentioned quaternary ammonium salt, as an essential ingredient, at a concentration of from 0.01 to 60% by weight.

The compound of the present invention may be applied in an arbitrarily selected form such as aqueous solution, wettable powder, granules, dust, emulsion, oil or paste. Therefore other additives, for example, salts, surfactants, thickeners and carriers may be added thereto depending on the selected formulation.

Examples of the salts include metal salts of carboxylic acids, such as succinates, malonates, citrates, gluconates and glutarates, metal salts of phosphoric acid compounds such as tripolyphosphates and hexametaphosphates and inorganic salts such as $Na_2SO_4$ and $MgSO_4$. Either one of these salts or a mixture thereof may be employed.

As the surfactants, nonionic and anionic surfactants may be used. Examples of the nonionic and/or anionic surfactants include nonionic surfactants such as polyoxyethylene (hereinafter simply referred to as POE) alkyl (carbon atom number: 6-22) ethers, POE alkyl (carbon atom number: 4-18) phenol ethers, polyoxypropylene polyoxyethylene (block or random) alkyl ethers, POE phenylphenol ether, POE styrenated phenol ether and POE tribenzylphenol ether; and anionic surfactants such as ligninsulfonate salts, alkylbenzenesulfonate salts, alkylsulfonates salts, POE alkylsulfonate salts, POE alkylphenyl ether sulfonate salts, POE alkylphenyl ether phosphate salts, POE phenylphenol ether sulfonate salts, POE phenylphenol ether phosphate salts, naphthalenesulfonate salts, naphthalenesulfonic acid/formalin condensate, POE tribenzylphenol ether sulfonate salts and POE tribenzylphenylphenol ether phosphate salts. Either one of these surfactants or a mixture thereof may be used.

The content of each of these surfactants in the biocide may range from 0 to 20% by weight, preferably from 1 to 10% by weight.

As a water-soluble thickener, either natural, semisynthetic or synthetic ones may be used. Examples of the natural thickeners include xanthan gum and Zanflo originating from microorganisms and pectin, gum arabic and guar gum originating from plants. Examples of the semisynthetic thickeners include methylated products, carboxyalkylated products and hydroxyalkylated products of cellulose or starch derivatives (including methylcellulose, carboxymethyl-cellulose and hydroxymethylcellulose) and sorbitol. Examples of the synthetic thickeners include polyacrylate salts, polymaleate salts, polyvinylpyrrolidone and EO adduct of pentaerythritol. These water-soluble thickeners may be used in the biocide in an amount of from approximately 0 to 3.0% by weight, preferably form approximately 0.05 to 0.5% by weight.

As the carrier, inorganic mineral salts and water-insoluble polymers may be employed. Examples of the inorganic mineral salts include inorganic salt clay, talc, bentonite, calcium carbonate, diatomaceous earth and white carbon. Examples of the water-insoluble polymers include styrenesulfonic acid, 2-acrylamide, 2-methylpropanesulfonic acid, xylenesulfonic acid, naphthalenesulfonic acid and polymers of salts thereof. Further, copolymers obtained by copolymerizing the above-mentioned copolymer with a hydrophobic monomer such as an alkyl acrylate, an alkyl methacrylate, vinyl alkyl ethers, vinyl acetate, ethylene, propylene, butylene, butadiene, diisobutylene, vinyl chloride, vinylidene chloride, acrylonitrile or styrene; or a hydrophilic monomer such as acrylic acid, methacrylic acid, maleic acid, fumaric acid, maleic anhydride, vinyl alcohol, acrylamide, methacrylamide, diacetone acrylamide or N-vinylpyrrolidone may be employed.

Now examples of the biocide to be activated by the biocide activator of the present invention will be given. However it is to be understood that the present invention is not restricted thereby. The biocide activator of the present invention produces no chemical injury to various crops and thus can be safely applied.

Examples of bactericides include Dithane (zinc ethylenebisdithiocarbamate), Maneb (manganese ethylenebisdithiocarbamate), Thiuram [bis(dimethylthiocarbamoyl) disulfide], Manzeb (zinc/manganese ethylenebisdithiocarbamate), Bisdaithane (bisdimethyldithiocarbamoylzinc ethylenebisdithiocarbamate), Propineb (zinc propylenebisdithiocarbamate), benzimidazole derivatives such as Benomyl [methyl 1-(butylcarbamoyl)-2-benzimidazolecarbamate) and Thiophanate-methyl[1,2-bis(3-methoxycarbonyl-2-thioureido)benzene], as well as Vinclozolin [3-(3,5-dichlorophey1)-5-methyl-5-vinyl-1,3-oxazolidine-2,4-dione], Iprodione [3-(3,5-dichlorophenyl)-N-isopropyl-2,4-dioxoimidazolidine-1-carboxamide], procymidone ®. [N-(3,5-dichlorophenyl)-1,2-dimethylcyclopropane-1,2-dicarboximide], Triazine [2,4-dichloro-6-(2-chloroanilino) 1,3,5-triazine], triflumizole ®. [(E) 4-chloro-α,α,α-trifluoro-N-(1-imidazol-1-yl-2-propoxyethylidane)-o-toluidine], Metalaxyl [methyl N-(2-methoxyacetyl)-N-(2,6-xylyl)-D,L-araninate], bitertanol ® [all-rac-1-(biphenyl-4-yloxy)-3,3-dimethyl-1-(1H-1,2,4-triazol-1-yl)2-butan-2-ol], triadimefon ® [1-(4-chlorophenoxy)- 3,3-dimethyl-1-(1,2,4-triazol-1-yl)-2-butanonel, Isoprothiolane (diisopropyl 1,3-dithiolan-2-ylidenemalonate), Daconil (tetrachloroisophthalonitrile), Pansoil ® (5-ethoxy-3-trichloromethyl-1,2,4-thiadiazole), Rabcide (4,5,6,7-tetrachlorophthalolide), Kitazin P (0,0-diisopropyl-S-benzyl thiophosphate), Hinosan (0-ethyl-S,S-diphenyl thiophosphate), probenzol ® (3-allyloxy-1,2-benzisothiazole 1,1-dioxide) and Captan (N-trichloromethylthiotetrahydrophthalimide).

Examples of insecticides include pyrethroid insecticides such as Fenvalerate [α-cyano-3-phenoxybenzyl 2-(4-chlorophenyl)-3-methylbutanoate) and Baytroid [cyano-4-fluoro-3-phenoxyphenylmethyl 3-(2,2-dichloroethenyl)-2,2-dimethylcyclopropanecarboxylate); organophosphorus insecticides such as DDVP (dimethyl 2,2-dichlorovinyl phosphate), Sumithion [0,0-dimethyl-0-(3-methyl-4-nitrophenyl) thiophosphate], Malathon (S-[1,2-bis(ethoxycarbonyl)ethyl] dimethyl phosphorothionate), Dimethoate [dimethyl S-(N-methylcarbamoylmethyl) dithiophosphate], Elsan (S-[α-ethoxycarbonyl)benzyl] dimethyl phosphorothiolthionate) and Baycid [0,0 dimethyl 0(3-methyl 4-methylthiophenyl) thiophosphate]; carbamate insecticides such as Bassa (0-butylphenyl methylcarbamate), MTMC (m-tolyl methylcarbamate), Meobal (3,4-dimethylphenyl N-methylcarbamate) and NAC (1-naphthyl N-methylcarbamate); as well as Methomyl (S-methyl-N-[(methylcarbamoyl)oxylthioacetimide) and Cartap [1,3-bis(carbamoylthio)-2-(N,N-dimethylamino)propane hydrochloride.

Examples of acaricides include Smite ® (2-[2-p-tert-butylphenoxy)isopropoxy] isopropyl 2-chloroethyl sulfide), Acricid (2,4-dinitro-6-sec-butylphenyl dimethylacrylate), Chlormite ® (isopropyl 4,4-dichlorobenzilate), Akar (ethyl 4,4-dichlorobenzilate), Kelthane [1,1-bis(p-chlorophenyl)-2,2,2-trichloroethanol), Citrazon (ethyl 0-benzoyl-3-chloro-2,6-dimethoxybenzohydroxymate), Omite [2-(p-tert-butylphenoxy)cyclohexyl 2-propynyl sulfite], Osadan [hexakis(β,β-dimethylphenylethyl)distannoxane], hexithiazox ® [trans-5-(4-chlorophenyl)-N-cyclohexyl-4-methyl-2-oxothiazolidine-3-carboxamide] and Amitraz [3-methyl-1,5-bis(2,4-xylyl)-1,3,5-triazapenta-1,4-diene].

Examples of herbicides include Stam (3,4-dichloropropionanilide), Saturn [S-(4-chlorobenzyl) N,N-diethylthiolcarbamate], Glyphosate [N-(phosphonomethyl)glycine isopropylamine salt], DCMU [3-(3,4-dichlorophenyl)-1,1-dimethylureal and Glamoxone (1,1-dimethyl-4,4'-dipyridium dichloride).

Furthermore, specific plant growth regulators such as MH (maleic acid hydrazide and Ethrel (2-chloroethylphosphonic acid) may be used.

The biocide composition of the present invention may further contain one or more plant growth regulators, fertilizers and/or preservatives.

The biocide activator of the present invention may be added to each of the aforesaid compositions and formulated. Alternately, it may be diluted at the time of use. The effect of avoiding the resistance against biocides, according to the present invention, may be achieved by employing each of these methods.

The mechanism of how such remarkable effects of the present inventions biocides activator enhances biocidal effects and avoids biocide-resistance is achieved has not been clarified as yet in detail. However, it is assumed, for example, that the biocide activator of the present invention is adsorbed by the cell membrane of a bacterium and thus disturbs the permeable function of the membrane or inhibits the activity of membrane-bonded enzymes localized on the surface of the bacterium, thus damaging the bacterium and reducing the resistance thereof against biocides. Thus the effect of avoiding biocide resistance can be achieved. Similar phenomena might be observed in the case of insecticides and acaricides.

Examples

To further illustrate the present invention, and without in any way limiting the invention, the following Examples are provided be given.

Table 1 shows the quaternary ammonium salts of the compound of the present invention and Formulation Examples will be given thereafter.

TABLE 1

| Cpd. No. | Counter ion | Quaternary ammonium |
|---|---|---|
| 1 | naphthalenesulfonic acid/formalin condensate (MW = 1000) |  |
| 2 | polystyrenesulfonic acid (MW = 10000) | |
| 3 | polyacrylic acid (MW = 3000) | 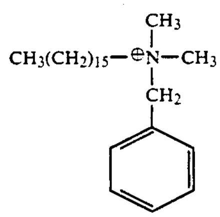  |
| 4 | methacrylic acid/styrene-sulfonic acid copolymer (MW = 10000) | |
| 5 | acrylic acid/maleic acid copolymer (MW = 8000) | |

Note:
MW represents average molecular weight.

| | |
|---|---|
| Formulation Example 1 | |
| compound No. 1 | 30 (parts by weight) |
| polyoxyethylene nonylphenyl ether (Emulgen 909, mfd. by Kao) | 5 |
| isopropyl alcohol | 65 |
| Formulation Example 2 | |
| compound No. 2 | 30 (parts by weight) |
| polyoxyethylene nonylphenyl ether (Emulgen 909, mfd. by Kao) | 5 |
| isopropyl alcohol | 65 |
| Formulation Example 3 | |
| compound No. 3 | 30 (parts by weight) |
| polyoxyethylene nonylphenyl ether (Emulgen 909, mfd. by Kao) | 5 |
| isopropyl alcohol | 65 |
| Formulation Example 4 | |
| compound No. 4 | 30 (parts by weight) |
| polyoxyethylene nonylphenyl ether (Emulgen 909, mfd. by Kao) | 5 |
| isopropyl alcohol | 65 |
| Formulation Example 5 | |
| compound No. 5 | 30 (parts by weight) |
| polyoxyethylene nonylphenyl ether (Emulgen 909, mfd. by Kao) | 5 |
| isopropyl alcohol | 65 |
| Formulation Example 6 | |
| compound No. 1 | 30 (parts by weight) |
| sodium ligninsulfonate | 2 |
| polyoxyethylene nonylphenyl ether | 5 |

-continued

| | |
|---|---|
| (Emulgen 911, mfd. by Kao) | |
| clay | 38 |
| bactericide (Benomyl) | 25 |
| Formulation Example 7 | |
| compound No. 2 | 30 (parts by weight) |
| clay | 50 |
| polyoxyethylene fatty acid ester | 10 |
| insecticide (Supracid) | 15 |
| potassium nonylphenyl ether sulfate salt (Levenol WZ, mfd. by Kao) | 5 |
| Formulation Example 8 | |
| compound No. 5 | 20 (parts by weight) |
| clay | 45 |
| polyoxyethylene sorbitan ester (Rheodol TW-0-120, mfd. by Kao) | 5 |
| polyoxyethylene nonylphenyl ether | 5 |
| acaricide (Osadan) | 20 |
| Comparative Formulation Example 1 | |
| sodium ligninsulfonate | 2 |
| polyoxyethylene nonylphenyl ether (Emulgen 911, mfd. by Kao) | 5 |
| fine clay powder (mfd. by Kunimine Kogyo) | 68 |
| Bactericide (Benomyl) | 25 |
| Comparative Formulation Example 2 | |
| polyoxyethylene fatty acid ester | 10 |
| sodium nonylphenyl ether sulfate (Levenol WZ, mfd. by Kao) | 5 |
| insecticide (Supracid) | 15 |
| fine clay powder (mfd. by Kunimine Kogyo) | 70 |
| Comparative Formulation Example 3 | |
| polyoxyethylene sorbitan ester (Rheodol TW-0-120, mfd. by Kao) | 5 |
| polyoxyethylene nonylphenyl ether | 5 |
| fine clay powder (mfd. by Kunimine Kogyo) | 55 |
| acaricide (Osadan) | 20 |

EXAMPLE 1

10 ml/pot of a spore suspension ($10^7$/ml) of Botrytis cinerea, which was resistant against bactericides, was applied to young cucumber seedlings at the trifoliate stage. Next, the seedlings were allowed to stand at 25° C. under a relative humidity of 90% for one day. In Test Examples 1 to 5, the biocide activators obtained in the above Formulation Examples 1 to 5 were added to a solution of marketed Benomyl (active ingredient concentration: 250 ppm) in such a manner as to dilute each of the activator 1000-fold. In Test Example 6 and Comparative Test Examples 1 and 2, on the other hand the dilution effected in such a manner as to provide the content with 250 ppm of the active ingredient, Benomyl. Then each of the obtained samples was applied in a dose of 5 ml per pot. In Comparative Test Example 3, the procedure of Test Example 1 was repeated except that no Benomyl was added.

Next, the seedlings were allowed to stand at 25° C. under a relative humidity of 85%. After 4 days, the lesions thus formed on each seedling were counted and the preventive value based on the control lot was calculated in accordance with the following equation:

$$\text{preventive value} = \left(1 - \frac{\text{lesion number of test lot}}{\text{lesion number of control lot}}\right) \times 100$$

Table 2 shows the results.

TABLE 2

| Test Example | Biocide activator Formulation Example | Dilution | Agrohorticultural bactericide Marketed Benomyl preparation | Active ingredient content of Benomyl at application (ppm) | Preventive Value |
| --- | --- | --- | --- | --- | --- |
| 1 | 1 | 1000-fold | separately added | 250 | 98 |
| 2 | 2 | 1000-fold | separately added | 250 | 100 |
| 3 | 3 | 1000-fold | separately added | 250 | 98 |
| 4 | 4 | 1000-fold | separately added | 250 | 98 |
| 5 | 5 | 1000-fold | separately added | 250 | 100 |
| 6 | 6 | 1000-fold | none (contained in preparation) | 250 | 98 |
| Comp. Test Example | | | | | |
| 1 | Comp. Formulation Example 1 | 1000-fold | none (contained in preparation) | 250 | 75 |
| 2 | none | — | added | 250 | 67 |
| 3 | Formulation Example 1 | 1000-fold | none | 0 | 35 |

EXAMPLE 2

The efficiency of an insecticide (Supracid) was examined by the Chinese cabbage leaf dipping method with the use of Myzus persicae Sulzer imagines (each lot having 30 imagines) by three times.

The preventive value was determined based on the data of a control lot.

In Test Examples 1 to 5, the biocide activators obtained in Formulation Examples 1 to 5 were mixed with a 180 ppm solution of marketed Supracid in such a manner as to dilute each of the activators 1000-fold. In Test Example 6 and Comparative Test Examples 1 and 2, on the other hand, the dilution was effected in such a manner as to provide a content with 180 ppm of supracid as the active ingredient. In Comparative Test Example 3, the procedure of Test Example 2 was repeated except no Supracid was added.

Table 3 shows the results.

EXAMPLE 3

Acaricidal effects were examined in a field, wherein Panonychus citri McGregor resistant against a marketed acaricide (Osadan) bred, by using three Citrus unshu trees per lot.

In Test Examples 1 to 5, the biocide activators obtained in Formulation Examples 1 to 5 were mixed with a 125 ppm solution of the marketed Osadan in such a manner as to dilute each of the activators 1000-fold. In Test Example 6 and Comparative Test Examples 1 and 2, on the other hand, the dilution was effected in such a manner as to provide a content with 125 ppm of Osadan as the active ingredient. In Comparative Test Example 3, the procedure of Test Example 1 was repeated except no Osadan was added.

Then 3, 10, 20 and 30 days after the treatment with the chemicals, mites on 30 leaves per tree were counted and the preventive value of each lot was calculated based on the data obtained in the control lot.

Table 4 shows the results.

TABLE 3

| Test Example | Biocide activator Formulation Example | Dilution | Agrohorticultural bactericide Marketed Supracid preparation | Active ingredient content of Supracid at application (ppm) | Preventive Value |
| --- | --- | --- | --- | --- | --- |
| 1 | 1 | 1000-fold | separately added | 180 | 100 |
| 2 | 2 | 1000-fold | separately added | 180 | 100 |
| 3 | 3 | 1000-fold | separately added | 180 | 100 |
| 4 | 4 | 1000-fold | separately added | 180 | 100 |
| 5 | 5 | 1000-fold | separately added | 180 | 100 |
| 6 | 7 | 1000-fold | none (contained in preparation) | 180 | 100 |
| Comp. Test Example | | | | | |
| 1 | Comp. Formulation Example 2 | 1000-fold | none (contained in preparation) | 180 | 66 |
| 2 | — | — | added | 180 | 60 |
| 3 | Formulation Example 2 | 1000-fold | none | 0 | 23 |

TABLE 4

| | Biocide activator Formulation Example | Dilution | Agrohorticultural acaricide Marketed Osadan preparation | Active ingredient content of Osadan at application (ppm) | Preventive Value |
| --- | --- | --- | --- | --- | --- |
| Test | Formulation | | | | |

TABLE 4-continued

| | Biocide activator | | Agrohorticultural acaricide | Active ingredient content of Osadan | |
|---|---|---|---|---|---|
| Example | Formulation Example | Dilution | Marketed Osadan preparation | at application (ppm) | Preventive Value |
| Example | Example | | | | |
| 1 | 1 | 1000-fold | separately added | 125 | 99 |
| 2 | 2 | 1000-fold | separately added | 125 | 99 |
| 3 | 3 | 1000-fold | separately added | 125 | 97 |
| 4 | 4 | 1000-fold | separately added | 125 | 100 |
| 5 | 5 | 1000-fold | separately added | 125 | 100 |
| 6 | 6 | 1000-fold | none (contained in preparation) | 125 | 98 |
| Comp. Test Example | | | | | |
| 1 | Comp. Formulation Example 1 | 1000-fold | none (contained in preparation) | 125 | 45 |
| 2 | none | — | separately added | 125 | 46 |
| 3 | Formulation Example 3 | 1000-fold | none | 0 | 38 |

EXAMPLE 4

The chemical injury of each compound to be used in the biocide activator of the present invention on plants was examined in the following manner. Namely, cucumber, kidney bean, tomato, eggplant and strawberry plants were grown in a green-house and the chemical injury of the compound to fruits and leaves of these crops was examined.

Table 5 shows the results.

TABLE 5

| | | Test crop | | | | |
|---|---|---|---|---|---|---|
| Test Example | Dilution | cucumber | kidney bean | tomato | eggplant | strawberry |
| Compound of the invention | | | | | | |
| 1 | ×1000 | none | none | none | none | none |
| | ×500 | none | none | none | none | none |
| 2 | ×1000 | none | none | none | none | none |
| | ×500 | none | none | none | none | none |
| 3 | ×1000 | none | none | none | none | none |
| | ×500 | none | none | none | none | none |
| 4 | ×1000 | none | none | none | none | none |
| | ×500 | none | none | none | none | none |
| 5 | ×1000 | none | none | none | none | none |
| | ×500 | none | none | none | none | none |

RESULTS

As the Examples 1 to 4 show, the biocide activator of the present invention apparently enhances biocidal effects without causing any chemical injury to crops.

We claim:

1. A biocide composition which consisting essentially of a biocide and 0.01 to 60% of an auxiliary compound, which is in a biocidally enhancing amount having the formula (I)

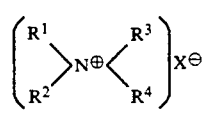

wherein at least one of $R^1$, $R^2$, $R^3$ represents a straight-chain or branched alkyl or alkenyl group having 8 to 30 carbon atoms while other(s) represent a group or a combination selected from among

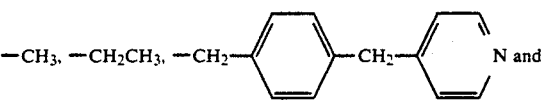

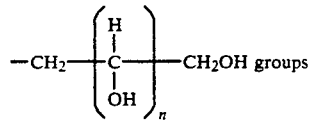

(wherein n ranges from 1 to 5;
$R^4$ represents a —CH$_3$ or —CH$_2$CH$_3$ group; and wherein counter ion $X^\ominus$ is an anion residue of an acid of an anionic oligomer or polymer having an average molecular weight of from 300 to 20,000, wherein the anionic oligomer or polymer is selected from the group consisting of a polymer comprising one or more monomers selected from the group consisting of unsaturated carboxylic acids and derivatives thereof; a polymer comprising styrenesulfonic acid and a formalin condensate of a sulfonate of a polycyclic aromatic compound along or having a hydrocarbon group as a substituent.

2. An aqueous-biocide solution or as recited in claim 1 consisting essentially of water.

3. The biocide of claim 1, wherein the average molecular weight of the polymer is from 1,000 to 10,000.

* * * * *